US009483611B2

(12) United States Patent
Otvos et al.

(10) Patent No.: US 9,483,611 B2
(45) Date of Patent: Nov. 1, 2016

(54) PROTECTIVE HDL PARTICLE NUMBER EVALUATIONS

(71) Applicant: LipoScience, Inc., Raleigh, NC (US)

(72) Inventors: James D. Otvos, Cary, NC (US); Irina Y. Shalaurova, Cary, NC (US)

(73) Assignee: LIPOSCIENCE, INC., Raleigh, NC (US)

(*) Notice: Subject to any disclaimer, the term of this patent is extended or adjusted under 35 U.S.C. 154(b) by 523 days.

(21) Appl. No.: 13/871,788

(22) Filed: Apr. 26, 2013

(65) Prior Publication Data

US 2013/0289884 A1 Oct. 31, 2013

Related U.S. Application Data

(60) Provisional application No. 61/639,508, filed on Apr. 27, 2012.

(51) Int. Cl.

| | |
|---|---|
| ***G01N 33/48*** | (2006.01) |
| ***G01N 33/50*** | (2006.01) |
| ***G06F 19/00*** | (2011.01) |
| ***G01N 33/92*** | (2006.01) |

(52) U.S. Cl.

CPC ............... *G06F 19/30* (2013.01); *G01N 33/92* (2013.01); *G06F 19/34* (2013.01); *G06F 19/3437* (2013.01); *G06F 19/3443* (2013.01)

(58) Field of Classification Search

None

See application file for complete search history.

(56) References Cited

U.S. PATENT DOCUMENTS

| | | | |
|---|---|---|---|
| 4,933,844 | A | 6/1990 | Otvos |
| 6,617,167 | B2 | 9/2003 | Otvos et al. |
| 7,250,304 | B2 | 7/2007 | Fogelman et al. |
| 7,491,543 | B2 | 2/2009 | Barzilai |
| 7,723,045 | B2 | 5/2010 | Fogelman et al. |
| 7,771,954 | B2 | 8/2010 | Hazen et al. |
| 8,013,602 | B2 | 9/2011 | Otvos et al. |
| 8,386,187 | B2 | 2/2013 | Otvos |
| 2004/0229275 | A1 | 11/2004 | Hayden et al. |

(Continued)

FOREIGN PATENT DOCUMENTS

| | | |
|---|---|---|
| WO | WO 00/51054 | 8/2000 |
| WO | WO 2011/153271 A1 | 12/2011 |
| WO | WO 2012/045773 A1 | 4/2012 |

OTHER PUBLICATIONS

Farmer et al. "Evolving Concepts of the Role of High-Density Lipoprotein in Protection from Atherosclerosis", *Curr Atheroscler Rep.*, (2011) 13:107-114.

(Continued)

*Primary Examiner* — Russell S Negin

(74) *Attorney, Agent, or Firm* — Kilpatrick Townsend & Stockton LLP

(57) ABSTRACT

Embodiments of the invention are directed to improved discrimination of protective (anti-atherogenic) HDL from atherogenic or non-protective (NP) HDL. The methods, systems and computer program products determine protective high density lipoprotein particle (HDL-P) numbers. The methods include obtaining concentration measurements of at least twenty subpopulations of HDL-P subclasses in a blood plasma or serum sample and calculating a protective HDL-P number using (i) a defined subset of the obtained HDL-P concentration measurements or (ii) a zero or defined weighting factor below 1 for HDL-P concentration measurements for HDL subclasses associated with particle sizes above about 11 nm.

18 Claims, 17 Drawing Sheets

(56) References Cited

U.S. PATENT DOCUMENTS

| | | | |
|---|---|---|---|
| 2005/0244892 | A1 | 11/2005 | Lazar et al. |
| 2007/0264677 | A1 | 11/2007 | Otvos |
| 2010/0285517 | A1 | 11/2010 | Hazen et al. |
| 2011/0124031 | A1 | 5/2011 | Hazen et al. |
| 2011/0201947 | A1 | 8/2011 | Hazen et al. |

OTHER PUBLICATIONS

Fogelman "When good cholesterol goes bad", *Nature Medicine*, vol. 10, No. 9, Sep. 2004, 902-903.

Jensen et al. "Apolipoprotein C-III as a Potential Modulator of the Association Between HDL-Cholesterol and Incident Coronary Heart Disease", *J Am Heart Assoc.* 2012;1:e000232 doi: 10.1161/JAHA.111.000232, 10 pages.

Jeyarajah et al. "Lipoprotein particle analysis by nuclear magnetic resonance spectroscopy", *Clin Lab Med*, Dec. 2006;26(4):847-870 (Abstract Only).

Kaess et al. "Large-Scale Candidate Gene Analysis of HDL Particle Features", *PLoS ONE*, Jan. 2011, vol. 6, Issue 1, e14529, 9 pages.

Kaess et al. "The lipoprotein subfraction profile: heritability and identification of quantitative loci", *Journal of Lipid Research*, vol. 49, 2008, 715-723.

Khera et al. "Cholesterol Efflux Capacity, High-Density Lipoprotein Function, and Atherosclerosis", *N Engl J Med*, 2011;364:127-135.

Navab et al. "HDL and cardiovascular disease: atherogenic and atheroprotective mechanisms", *Nat Rev Cardiol*, Apr. 2011;8(4)222-232 (Abstract Only).

Sacks et al. "Cardiovascular Endocrinology 4. Low-Density Lipoprotein Size and Cardiovascular Disease: A Reappraisal", *The Journal of Clinical Endocrinology & Metabolism*, 88(10):4525-4532, 2003.

Soininen et al. "High-throughput serum NMR metabonomics for cost-effective holistic studies on systemic metabolism", *The Royal Society of Chemistry, Analyst*, 2009, 134, 1781-1785.

Suna et al. "H NMR metabonomics of plasma lipoprotein subclasses: elucidation of metabolic clustering by self-organising maps", *NMR Biomed.*, 2007, 20: 658-672.

van der Steeg et al. "High-Density Lipoprotein Cholesterol, High-Density Lipoprotein Particle Size, and Apolipoprotein A-I: Significance fro Cardiovascular Risk", *Journal of the American College of Cardiology*, vol. 51, No. 6, 2008, 634-642.

Wilson et al. "Impact of national guidelines for cholesterol risk factor screening. The Framingham Offspring Study", *JAMA*, Jul. 7, 1989; 262(1):41-44 (Abstract Only).

Garvey et al., "Effects of Insulin Resistance and Type 2 Diabetes on Lipoprotein Subclass Particle Size and Concentration Determined by Nuclear Magnetic Resonance" Diabetes Feb. 2003, 52: 453-462.

Pascot et al., "Reduced HDL Particle Size as an Additional Feature of the Atherogenic Dyslipdemia of Abdominal Obesity" Journal of Lipid Research 2001, 42:2007-2014.

Syvanne et al., "High Density Lipoprotein Subfractions in Non-insulin Dependent Diabetes mellitus and Coronary Artery Disease" Journal of Lipid Research 1995, 36: 573-582.

United States Patent and Trademark Office, Office Action, U.S. Appl. No. 13/871,873 dated Nov. 12, 2015.

United States Patent and Trademark Office, Office Action, U.S. Appl. No. 13/871,873 dated Mar. 10, 2015.

H26 —— H21

NON-PROTECTIVE L-HDL

POTENTIAL "PROTECTIVE" HDL-P PARAMETERS (P-HDL-Ps)

| | HDL-P | P1-HDL-P | P2-HDL-P | P3-HDL-P | P4-HDL-P |
|---|---|---|---|---|---|
| SUBCLASS COMPONENTS OF HDL-P (SUMMED) | WEIGHTING FACTOR | WEIGHTING FACTOR | WEIGHTING FACTOR | WEIGHTING FACTOR | WEIGHTING FACTOR |
| $HDL_{26-21}$ | 1.0 | 0.0 (OMIT) | 0.0 (OMIT) | 0.0 (OMIT) | 0.0 (OMIT) |
| $HDL_{20-9}$ | 1.0 | 1.0 | 1.0 | 1.0 | 1.0 |
| $HDL_8$ | 1.0 | 0.0 (OMIT) | 1.0 | 0.0 (OMIT) | 1.0 |
| $HDL_{7-1}$ | 1.0 | 1.0 | 1.0 | 1.5 | 1.5 |
| MEDIAN (μmol/L) | 33.3 | 28.2 | 32.1 | 33.7 | 37.5 |
| INTERQUARTILE RANGE | 29.2-37.9 | 24.7-32.1 | 28.3-36.6 | 30.1-37.6 | 33.6-41.5 |
| CONTINUOUS ASSOCIATION WITH CHD* | | | | | |
| MODEL $\chi^2$ | 230.7 | 233.0 | 232.0 | 235.1 | 233.6 |
| PARAMETER $\chi^2$ | -3.8 | -6.1 | -5.1 | -8.2 | -6.7 |
| HR PER 1-SD | 0.869 | 0.837 | 0.854 | 0.827 | 0.843 |
| P VALUE | 0.050 | 0.014 | 0.023 | 0.004 | 0.010 |

*FROM COX REGRESSION IN MESA (289 CHD EVENTS) ADJUSTED FOR AGE, SEX, ETHNICITY, SMOKING,SBP, HYPERTENSION TREATMENT, BMI, DM, logTG, LDL-P

FIG. 7

POTENTIAL "ATHEROGENIC" OR NON-PROTECTIVE HDL-P PARAMETERS (A-HDL-Ps)

| | A1-HDL-P | A2-HDL-P |
|---|---|---|
| HDL SUBCLASS | $HDL_{26-21}$ | $HDL_{24-23}$ |
| MEDIAN (μmol/L) | 0.90 | 0.07 |
| INTERQUARTILE RANGE | 0.45-1.63 | 0-0.21 |
| CONTINUOUS ASSOCIATION WITH CHD* | | |
| MODEL $\chi^2$ | 235.9 | 236.7 |
| PARAMETER $\chi^2$ | +3.3 | +4.4 |
| HR PER 1-SD | 1.128 | 1.123 |
| P VALUE | 0.068 | 0.036 |
| DICHOTOMOUS ASSOCIATION WITH CHD* (HR) | | |
| HR (95%CI) >80$^{th}$ PERCENTILE | 1.09 (0.77-1.56) (p=0.62) | 0.94 (0.69-1.27) (p=0.68) |
| HR (95%CI) >90$^{th}$ PERCENTILE | 1.41 (0.89-2.22) (p=0.14) | 1.22 (0.84-1.78) (p=0.29) |
| HR (95%CI) >95$^{th}$ PERCENTILE | 1.60 (0.89-2.87) (p=0.12) | 1.21 (0.72-2.04) (p=0.47) |

*FROM COX REGRESSION IN MESA (289 CHD EVENTS) ADJUSTED FOR AGE, SEX, ETHNICITY, SMOKING, SBP, HYPERTENSION TREATMENT, BMI, DM, logTG, LDL-P, P1-HDL-P.

FIG. 8

CHD EVENT PREDICTION IN MESA BY ALTERNATE HDL BIOMARKERS

| | RELATIVE SUBCLASS WEIGHTING | | | CHD PREDICTION IN MESA* | | | |
|---|---|---|---|---|---|---|---|
| | VERY LARGE | LARGE/ MEDIUM | SMALL | HR PER 1 SD | MODEL $\chi 2$ | WALD $\chi 2$ | p |
| HDL-C | 4 | 1 | 0.4 | 0.933 | 227.2 | 0.7 | 0.42 |
| HDL-P | 1 | 1 | 1 | 0.869 | 230.7 | -3.8 | 0.05 |
| PROHDL-P (P3) | 0 | 1 | 1.5 | 0.827 | 235.1 | -8.2 | 0.004 |

*FROM COX REGRESSION MODELS ADJUSTED FOR AGE, SEX, ETHNICITY, SMOKING, SBP, HYPERTENSION TREATMENT, BMI, DIABETES, logTG, AND LDL-P

FIG. 9B

PROHDL-P APPEARS TO OFFER CLINICALLY MEANINGFUL IMPROVEMENT OVER HDL-P

| | $\chi^2$ MODEL | C-STATISTIC (AUC) | $\chi^2$ PARAMETER | P |
|---|---|---|---|---|
| BASE (8) | 211.0 | 0.747 | | |
| LDL-P | 228.4 | 0.752 | | |
| LDL-P + TG | 229.4 | 0.753 | 1.0 | 0.32 |
| LDL-P + TG + HDL-C | 230.0 | 0.753 | -0.72 | 0.40 |
| LDL-P + TG + HDL-P | 232.1 | 0.754 | -2.67 | 0.10 |
| LDL-P + TG + PROHDL-P | 234.4 | 0.756 | -4.83 | 0.03 |

FROM LOGISTIC REGRESSION MODELS FOR CHD EVENTS (n=289), ADJUSTED FOR AGE, SEX, RACE, SMOKING, SYSTOLIC BLOOD PRESSURE, HTNrx, BMI, AND DIABETES STATUS.

FIG. 9C

PROTECTIVE HDL PARTICLE NUMBER EVALUATIONS

RELATED APPLICATIONS

This application claims priority to and the benefit of U.S. Provisional Application Ser. No. 61/639,508, filed Apr. 27, 2012, the contents of which are hereby incorporated by reference as if recited in full herein.

FIELD OF THE INVENTION

The present invention relates generally to analysis of lipoproteins. The invention may be particularly suitable for analysis of lipoprotein constituents in blood plasma and serum.

BACKGROUND OF THE INVENTION

NMR spectroscopy has been used to concurrently measure very low density lipoprotein (VLDL), low density lipoproteins (LDL) and high density lipoproteins (HDL) as VLDL, LDL and HDL particle subclasses from in vitro blood plasma or serum samples. See, FIG. 1 and U.S. Pat. Nos. 4,933,844 and 6,617,167, the contents of which are hereby incorporated by reference as if recited in full herein. Generally stated, to evaluate the lipoproteins in a blood plasma and/or serum sample, the amplitudes of a plurality of NMR spectroscopy derived signals within a chemical shift region of the NMR spectrum are derived by deconvolution of the composite methyl signal envelope or spectrum to yield subclass concentrations.

The subclasses are represented by many (typically over 60) discrete contributing subclass signals associated with NMR frequency and lipoprotein diameter as shown in FIG. 2. As shown in FIG. 3A, the NMR evaluations can interrogate the NMR signals to produce concentrations of different subpopulations shown as seventy-three discrete subpopulations, 27 for VLDL, 20 for LDL and 26 for HDL. These sub-populations can be further characterized as associated with a particular size range within the VLDL, LDL or HDL subclasses.

Conventionally, a patient's overall risk of coronary heart disease (CHD) and/or coronary artery disease (CAD) has been assessed based on measurements of cholesterol content of a patient's LDL and HDL particles (LDL-C, HDL-C) rather than the numbers of these particles. These two risk factors are used to assess a patient's risk, and treatment decisions may be made to reduce the "bad" cholesterol (LDL-C) or increase the "good" cholesterol (HDL-C).

In the past, "advanced" lipoprotein test panels have typically included a total high density lipoprotein particle (HDL-P) measurement (e.g., HDL-P number) and a total low density lipoprotein particle (LDL-P) measurement (e.g., LDL-P number). The particle numbers represent the concentration in units such as nmol/L (for LDL-P) or μmol/L (for HDL-P). A total HDL-P number, the sum of the concentration values of each of the three sub-groups of HDL-P subclasses, can provide CHD risk assessment information that may be more accurate or complement HDL-C. It has also been proposed that large and small HDL particle subclasses do not confer the same anti-atherogenic potential. See, e.g., U.S. 2007/0264677, the contents of which are hereby incorporated by reference as if recited in full herein.

It is believed that LDL-P is a better indicator of risk of CHD relative to LDL-C as well as for therapy decisions. However, there are still open questions about the different functions of HDL and how to best evaluate CHD risk associated with a patient's HDL. See, e.g., Kher at el., *Cholesterol Efflux Capacity, High-Density Lipoprotein Function, and Athersclerosis*, N Engl. J. Med. 364: 127-135 (Jan. 13, 2011); Navab et al., *HDL and cardiovascular disease: atherogenic and atheroprotective mechanisms*, Nat. Rev. Cardiol., 8, 222-232 (2011); and Alan Fogelman, *When good cholesterol goes bad*, Nat. Med., Vol. 10, No. 9, pp. 902-903 (September 2004), the contents of which are hereby incorporated by reference as if recited in full herein.

The mechanisms by which HDL can be protective or non-protective as associated with a person's risk of developing atherosclerosis or heart disease are complex and multifactorial. See, Farmer et al., *Evolving Concepts of the Role of High-Density Lipoprotein in Protection from Athersclerosis*, Curr Atheroscler Rep (2011) 13:107-114, the contents of which are hereby incorporated by reference as if recited in full herein.

SUMMARY

Embodiments of the invention are directed to improved discrimination of protective (anti-atherogenic) HDL from atherogenic and/or non-protective (NP) HDL.

Certain embodiments of the present invention are directed at providing methods, systems, and computer program products that discriminate between subclasses of HDL particles of a discrete size range taken from a blood plasma or serum sample to facilitate patient risk stratification and allow more effective treatment decisions compared with use of conventional markers such as either LDL-based risk alone, total HDL-P (unadjusted), HDL cholesterol (HDL-C) or with the ratio of LDL-C/HDL-C.

Some embodiments are directed to methods of determining protective high density lipoprotein particle (HDL-P) numbers. The methods include obtaining concentration measurements of at least twenty subpopulations of HDL-P subclasses in a blood plasma or serum sample and calculating a protective HDL-P number using (i) a defined subset of the obtained HDL-P concentration measurements or (i) a zero or defined weighting factor below 1 for HDL-P concentration measurements for HDL subclasses associated with particle sizes above 11 nm.

The calculating step can be carried out electronically and can exclude HDL subpopulations with sizes above 11 nm.

The method can also include calculating a non-protective HDL-P number using HDL subclass particle concentrations excluded from the calculated protective HDL-P number.

The obtaining step can be carried out to obtain 26 subpopulation concentrations corresponding to H1 to H26, and the calculating of the protective HDL-P number can include summing concentration measurements of either: (i) H1 to H20 or (ii) H1 to H7 and H9 to H20.

The obtaining step can be carried out to obtain at least 26 discrete subpopulation concentrations of HDL-P with particle sizes between about 7 nm to about 14 nm, corresponding to H1 to H26, and the calculating the protective HDL-P number includes summing H1 to H7 concentrations, then applying a defined first weight above 1 to the summed concentration of H1 to H7 and summing the weighted H1-H7 concentration with a sum of H9-H20 concentrations (which may, in some embodiments, be unweighted or have a weight below the first weight).

The method may include generating a protective CHD lipoprotein parameter using the protective HDL-P number and a low density lipoprotein particle (LDL-P) number.

The method can include determining a subject's risk of having and/or developing CHD based, in part, on the protective HDL-P number.

The obtaining step can include obtaining NMR signal of an in vitro blood plasma or serum patient sample to determine NMR derived concentration measurements.

Other embodiments are directed to methods of determining a subject's risk of having and/or developing CHD. The methods include: (a) measuring concentrations of at least twenty different high density lipoprotein particle (HDL-P) subclasses with sizes between about 7 nm to about 14 nm of an in vitro blood plasma and/or serum sample of interest; and (b) determining a protective HDL-P particle number using only measured concentrations of particle sizes between about 7 nm and 11 nm.

The measuring step can be carried out to obtain at least 26 different concentrations associated with H1 to H26 and the determining uses either H1-H7 and H9-H20 or H1-H20.

Yet other embodiments are directed to methods for determining a subject's risk of CHD. The methods include: (a) obtaining greater than 20 NMR derived concentration measurements of subpopulations of small, medium and large high density lipoprotein (HDL) subclasses of a biosample of interest; (b) summing HDL particle concentration measurements of substantially all or all of HDL particle sizes between about 7.3 nm to about 10.8 nm; and (c) defining a protective HDL-P number based on the summing step.

The method can include applying a weighting factor to the small HDL particle concentrations before the summing step, then using the weighted small HDL particle concentrations in the summing step.

The obtaining, applying, summing and defining steps can be carried out using at least one processor.

The method can include: applying a zero or a defined reduced weight to or excluding concentration measurements of large HDL particle sizes of 11 nm or greater; and applying an increased weighting factor to the small HDL particle concentrations before the summing step, then using the weighted small and large HDL particle concentrations in the summing step.

The method can also include calculating a non-protective HDL-P number using concentrations of large HDL particle sizes of 11 nm or greater.

Still other embodiments are directed to computer program products for defining an improved protective HDL particle number associated with in vitro patient biosamples to assess anti-atherogenic protection and/or CHD risk. The computer program product includes a non-transitory computer readable storage medium having computer readable program code embodied in the medium. The computer-readable program code includes: (a) computer readable program code that obtains concentration measurements of at least twenty subpopulations of HDL-P subclasses in a blood plasma or serum sample; and (b) computer readable program code that calculates a protective HDL-P number using a defined subset of the obtained HDL-P concentration measurements or using a zero or defined weighting factor below 1 for HDL-P concentration measurements for HDL subclasses associated with particle sizes above 11 nm.

The computer program code that calculates the protective HDL-P number can be configured to exclude or apply a zero weight to HDL subpopulations with sizes between about 13.5 nm to about 11 nm.

The computer program product can also include computer program code that calculates a non-protective HDL-P number using HDL subclass particle concentrations excluded or give a zero weight from the calculated protective HDL-P number.

The computer program code that obtains the at least 20 subpopulations can be configured to obtain 26 subpopulation concentrations corresponding to H1 to H26 and the computer program code that calculates the protective HDL-P number can be configured to sum concentration measurements of either: (i) H1 to H20 or (ii) H1 to H7 and H9 to H20.

Still other embodiments are directed to systems for obtaining data regarding lipoprotein constituents. The systems include: (a) an NMR spectrometer for acquiring at least one NMR spectrum of an in vitro blood plasma or serum sample; and (b) a controller in communication with the NMR spectrometer, the controller configured to (i) obtain concentration measurements of at least twenty subpopulations of high density lipoprotein particle (HDL-P) subclasses in a blood plasma or serum sample and (ii) calculate a protective HDL-P number using (i) a defined subset of the obtained HDL-P concentration measurements or (ii) a zero or (other) defined weighting factor below 1 for HDL-P concentration measurements for HDL subclasses associated with particle sizes 11 nm and above.

Yet other embodiments of the invention are directed to a patient report that includes a plurality of lipoprotein measurements including a non-protective or atherogenic low density lipoprotein particle number (LDL-P), a protective high density lipoprotein particle (HDL-P) number in concentration units and a non-protective HDL-P number in concentration units.

Further features, advantages and details of the present invention will be appreciated by those of ordinary skill in the art from a reading of the figures and the detailed description of the preferred embodiments that follow, such description being merely illustrative of the present invention. Features described with respect with one embodiment can be incorporated with other embodiments although not specifically discussed therewith. That is, it is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. The foregoing and other aspects of the present invention are explained in detail in the specification set forth below.

As will be appreciated by those of skill in the art in light of the present disclosure, embodiments of the present invention may include methods, systems, apparatus and/or computer program products or combinations thereof.

BRIEF DESCRIPTION OF THE FIGURES

FIG. 7 is a chart of potential protective HDL-P parameters according to embodiments of the present invention.

FIG. 8 is a chart of potential non-protective HDL-P parameters according to embodiments of the present invention.

FIG. 9B is a chart of different HDL parameters and associated subclass weighting and CHD prediction in MESA derived from Cox regression models adjusted for age, sex, ethnicity, smoking, SBP, hypertension treatment, BMI, diabetes, log TG, and LDL-P according to embodiments of the present invention.

FIG. 9C is a chart that statistically compares prediction models that include either HDL-C, total HDL-P, or protective HDL-P as the HDL risk factor according to embodiments of the present invention.

Figure 1:
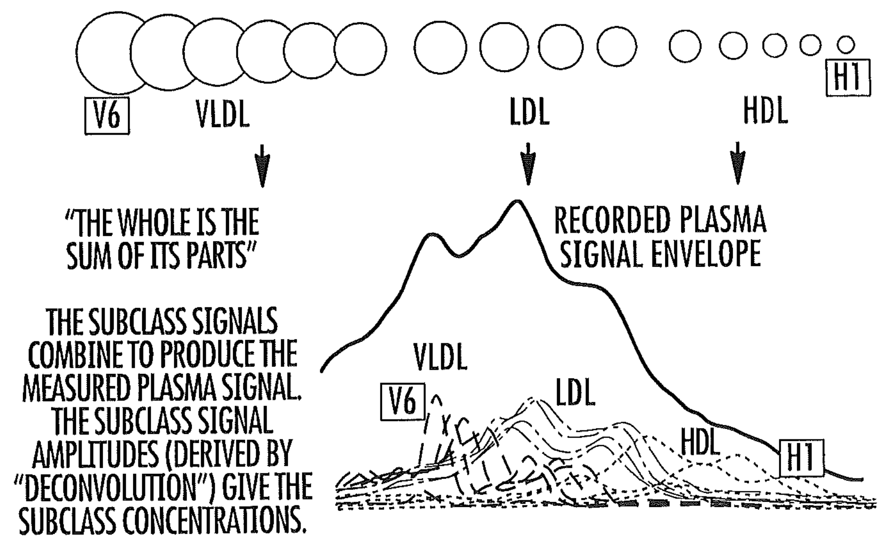
FIG. 1 is a schematic illustration of lipoprotein subclasses and the chemical shift spectra of a representative sample of lipoprotein constituent subclasses with a composite plasma signal envelope and subclass signals that can be used for subclass concentrations.

The foregoing and other objects and aspects of the present invention are explained in detail in the specification set forth below.

DETAILED DESCRIPTION OF EMBODIMENTS OF THE INVENTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "programmatically" means carried out using computer program directed operations. The terms "automated" and "automatic" means that the operations can be carried out with minimal or no manual labor or input. The term "semi-automated" refers to allowing operators some input or activation, but the calculations and signal acquisition as well as the calculation of the concentrations of the ionized constituent(s) is done electronically, typically programmatically, without requiring manual input. The term "about" refers to +/−10% (mean or average) of a specified value or number.

The terms CAD and CHD are used interchangeably to correspond to a patient or subject's risk of developing or having coronary artery and/or coronary heart disease, respectively.

The terms "population norm" and "standard" value associated with a lipoprotein measurement can be the values defined by a large study such as the Framingham Offspring Study or the Multi-Ethnic Study of Atherosclerosis (MESA). However, the instant invention is not limited to these population values as the presently defined normal and at-risk population values for LDL particle concentrations or levels may change over time.

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

As is generally accepted, HDL-cholesterol and/or LDL-cholesterol levels provided by conventional lipid panels fail to sufficiently differentiate populations with and without elevated risk for CHD or CAD. As is known to those of skill in the art, the Framingham study proposed a relatively lengthy risk model that considers many factors such as age, gender, smoking habits, as well as cholesterol values. The research conducted in the Framingham Offspring Study also defined normative and at-risk population values from subjects in the study. See Wilson et al., *Impact of National Guidelines for Cholesterol Risk Factor Screening. The Framingham Offspring Study*, JAMA, 1989; 262: 41-44.

Embodiments of the invention are directed to improved discrimination of protective (anti-atherogenic) HDL-P (which can be interchangeably referred to as "Pro HDL-P" or P-HDL-P) from atherogenic or non-protective (NP) HDL-P. The term "protective HDL-P" refers to HDL-P parameters that have a statistical probability of being inversely associated with risk of CHD and/or providing anti-atherogenic protection against one or more of atherosclerosis, CHD and/or myocardial infarction ("MI"). The term "NP-HDL" refers to HDL-P parameters which do not provide a statistical probability of inverse risk association for one or more of atherosclerosis, CHD or myocardial infarction (MI). The NP-HDL may be merely "neutral" as to being associated with an increased risk or may be considered atherogenic and provide an increased risk of atherosclerosis, CHD or MI.

Lipoproteins include a wide variety of particles found in plasma, serum, whole blood, and lymph, comprising various types and quantities of triglycerides, cholesterol, phospholipids, sphyngolipids, and proteins. These various particles permit the solubilization of otherwise hydrophobic lipid molecules in blood and serve a variety of functions related to lipolysis, lipogenesis, and lipid transport between the gut, liver, muscle tissue and adipose tissue.

In blood and/or plasma, HDL has been classified in many ways, generally based on physical properties such as density or electrophoretic mobility or measures of apolipoprotein A-1 (Apo A-1), the main protein in HDL. Classification based on nuclear magnetic resonance (NMR) determined particle size can distinguish a number of discrete components (subpopulations) for each of VLDL, HDL and LDL subclasses.

Figure 3:
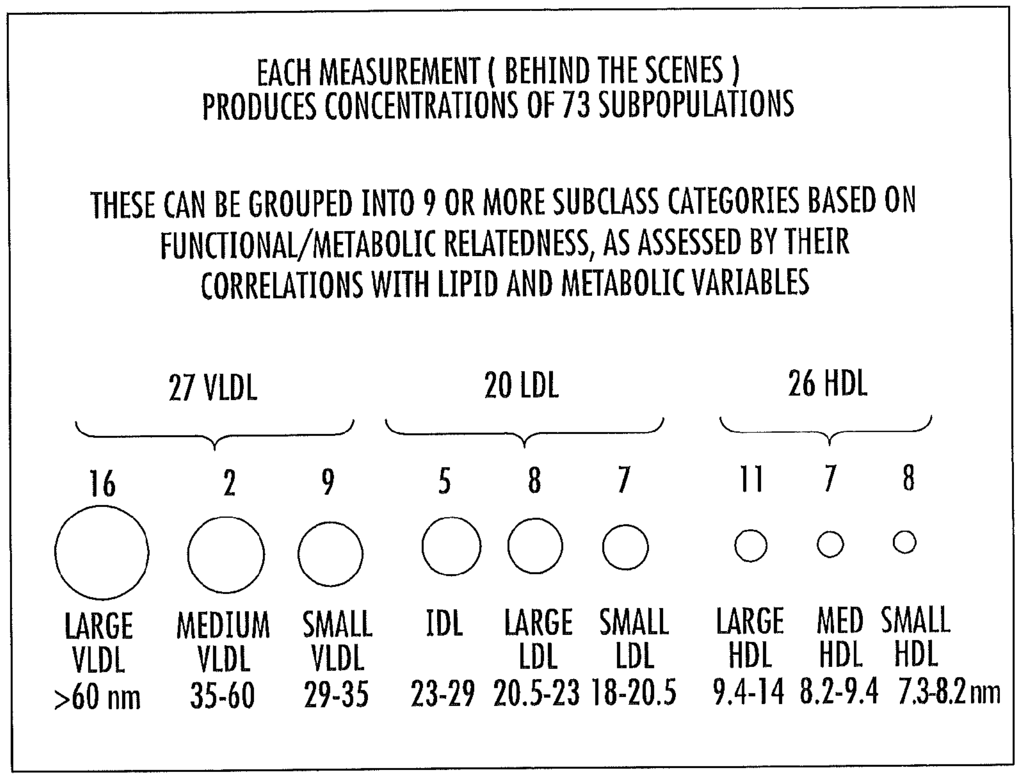
FIG. 3 is a schematic illustration showing how the 73 subpopulations may be grouped into 9 subclasses to maximize their associations with insulin resistance such as for LP-IR assessments.
Figure 4:
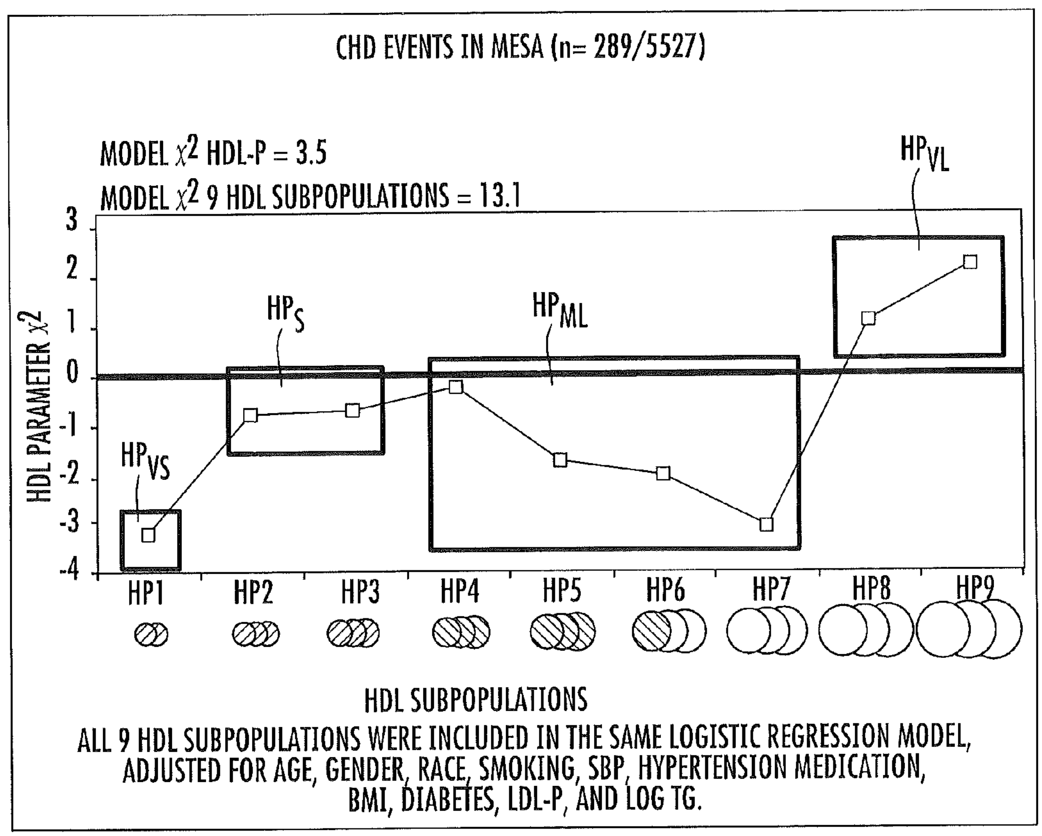
FIG. 4 is a graph illustrating CHD risk associations for each of 9 different size groupings of the 26 HDL subpopulations according to embodiments of the present invention.

Embodiments of the invention classify lipoprotein particles into subclasses grouped by size ranges based on functional/metabolic relatedness as assessed by their correlations with lipid and metabolic variables as shown in FIG. 4. The evaluations can measure over 20 discrete subpopulations (sizes) of lipoprotein particles, typically between about 30-80 different size subpopulations (or even more). These discrete sub-populations can be grouped into defined subclasses. The defined subclasses can include a plurality of different subclasses for VLDL, HDL and LDL (and which may include IDL as a separate subclass in the size range between LDL and small VLDL). The different subclasses typically include different numbers of sub-populations or components of different particle sizes within the subclass groupings. The large HDL subclass can include more discrete subpopulation measurements than either the medium or small HDL subclasses. The medium HDL subclass can include less sub-population components or measurements than either the large HDL or small HDL subclasses. Although FIG. 3 illustrates nine (9) different subclasses, three each for the VLDL, LDL and HDL subclasses, other subclass groupings of subpopulations may be used, such as four subclass groupings for HDL as will be discussed further below.

HDL-P sizes typically range (on average) from between about 7 nm to about 15 nm, more typically about 7.3 nm to about 14 nm. The HDL subclasses of different size can be quantified from the amplitudes of their spectroscopically distinct lipid methyl group NMR signals. See, Jeyarajah et al., *Lipoprotein particle analysis by nuclear magnetic resonance spectroscopy*, Clin Lab Med. 2006; 26: pp. 847-870, the contents of which are hereby incorporated by reference as if recited in full herein. The HDL-P concentration is the sum of the particle concentrations of all of the respective HDL subpopulations. The NMR derived HDL-P and LDL-P particle sizes noted herein typically refer to average measurements, but other size demarcations may be used. It is contemplated that the defined estimated ranges for one or more of the estimated diameters of the different subpopulations may vary by +/−0.1 nm or somewhat more, particularly when measured with alternative NMR deconvolving protocols or other methods.

It is also noted that while NMR measurements of the lipoprotein particles are contemplated as being particularly suitable for the analyses described herein, it is contemplated that other technologies may be used to measure these parameters now or in the future and embodiments of the invention are not limited to this measurement methodology. Also, other NMR protocols including other NMR deconvolving protocols from those described herein may also be used. See, e.g., Kaess et al., The lipoprotein subfraction profile: heritability and identification of quantitative trait loci, J. of Lipid Res. Vol. 49 pp. 715-723 (2008); and Suna et al., 1H NMR metabolomics of plasma lipoprotein subclasses: elucidation of metabolic clustering by self-organising maps, NMR Biomed. 2007; 20: 658-672. Examples of non-NMR methods include, for example, flotation and ultracentrifugation employing a density-based separation technique for evaluating lipoprotein particles. Ion mobility analysis is a different technology for measuring lipoprotein subclass particle concentrations.

LDL is known to carry the so-called "bad" cholesterol. LDL particles come in different sizes. Conventionally, the smaller sizes have been thought to be the most dangerous type in that they were generally thought to be inherently more atherogenic than large particles. See, Sacks et al., *Clinical review* 163*: Cardiovascular endocrinology: Low density lipoprotein size and cardiovascular disease: a reappraisal*, J. Clin. Endocrinol Metab., 2003; 88: 4525-4532. Presently, LDL particle sizes are characterized as "Pattern A" (large) and "Pattern B" (small). Pattern A can be defined as large average particle sizes which typically includes sizes of between about 20.5-23.0 nm. Pattern B can be defined as smaller average particle sizes between about 18.0-20.5 nm. The LDL-P number can be defined as the sum of the small, large and IDL subclass concentrations (FIG. 5A).

Figure 2:
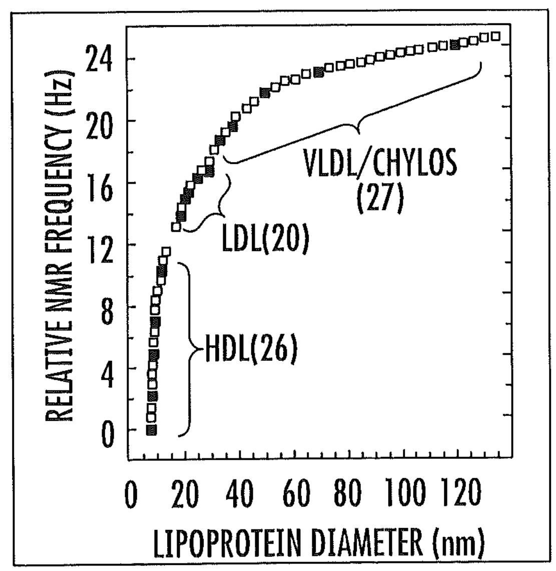
FIG. 2 is a graph of relative NMR frequency (Hz) versus lipoprotein diameter (nm) of HDL, LDL and VLDL/Chylos for 73 different subclass signals.
Figure 5A:
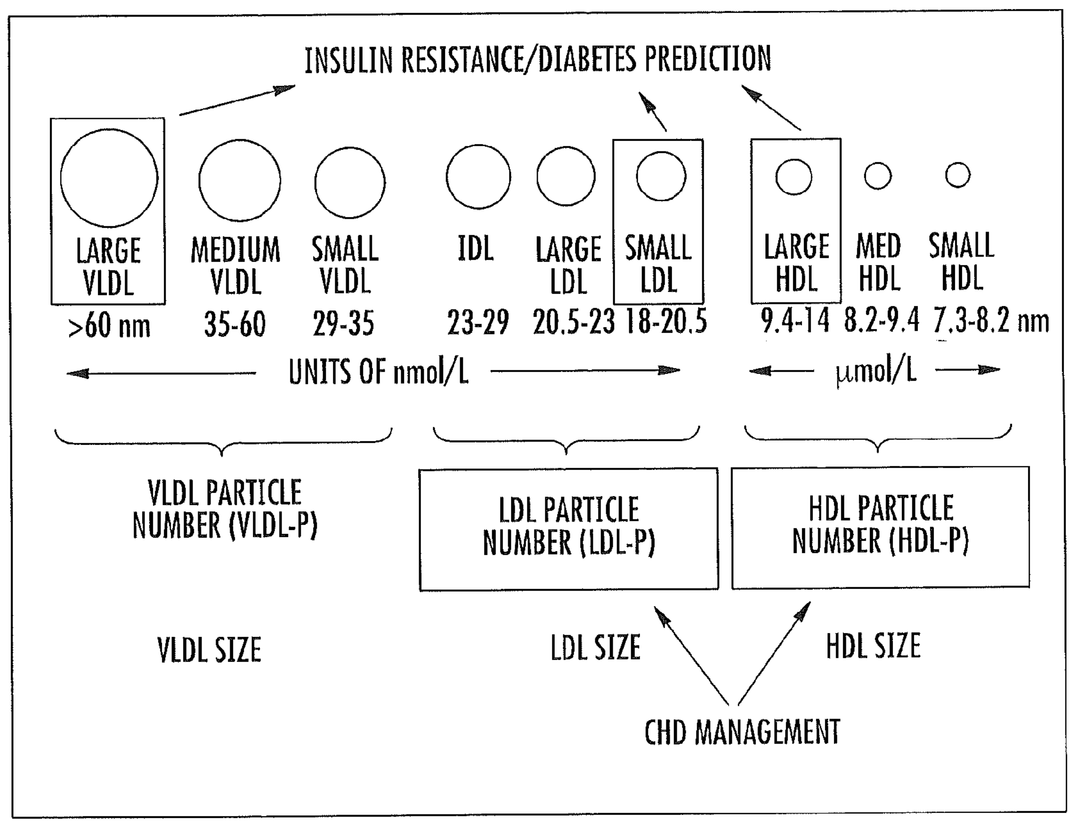
FIG. 5A is a schematic illustration of different lipoprotein parameters associated with insulin resistance/diabetes and/or CHD management according to embodiments of the present invention.

As shown in FIGS. 2, 3, and 5A, the small LDL particles can include particles whose sizes range from between about 18.0 to about 20.5 nm. The large LDL particles can include particles ranging in diameter between about 20.5-23.0 nm. It is noted that the LDL subclasses of particles can be divided in other size ranges. For example, small may be between about 18.0-20.5 nm, intermediate may be between about 20.5-21.2 nm, and large may be between about 21.2-23 nm. In addition, intermediate-density lipoprotein particles ("IDL" or "IDL-P"), which range in diameter from approximately 23.0-29.0 nm, can be included among the particles defined as LDL.

Embodiments of the invention can define a suitable number of HDL subpopulations, typically at least 20, more typically 26 HDL subpopulations between 7.3 nm or 7.4 nm to 13.5 nm or 14 nm.

In some embodiments, as shown in FIG. 3, the lipoprotein measurements can include 73 subpopulations: 26 for HDL, 20 for LDL and 27 for VLDL. However, other groupings, size ranges for a grouping, and/or numbers of discrete sub-population measurements may be used. The different subpopulations of HDL-P can be identified as in Table 1 by a number from 1-26, with "1" representing the smallest size HDL subpopulation and "26" being the largest size subpopulation in the HDL subpopulation category.

In some embodiments, the total number of HDL subpopulations can be grouped into nine groups, HP1-HP9, which can then be further grouped into four groupings shown by the four boxes in FIG. 4. The "four" subclass groupings can be defined as very large HDL subclasses ($HP_{VL}$), large and medium subclasses ($HP_{ML}$), small subclasses ($HP_S$), and very small subclasses ($HP_{VS}$). The four groupings are based on a statistical analysis of epidemiologic associations to determine how the various subpopulations should be grouped based on risk association with CHD (rather than LP-IR or insulin resistance or diabetes as described, for example, in U.S. Pat. No. 8,386,187, the content of which is hereby incorporated by reference as if recited in full herein).

FIG. 4 illustrates that H1-H20 (HP1-HP7 groupings) have negative risk association (the subclasses/subpopulations below the horizontal "0" $\chi 2$ line) while $HP_{VL}$ (H21-H26 or the HP8 and HP 9 groupings) have a positive risk association (the subclasses/subpopulations above the horizontal line).

FIG. 5A illustrates that conventional CHD risk assessment involves LDL-P and HDL-P numbers and that insulin resistance/diabetes prediction or risk is associated with concentrations of large VLDL, small LDL and large HDL.

Figure 5B:
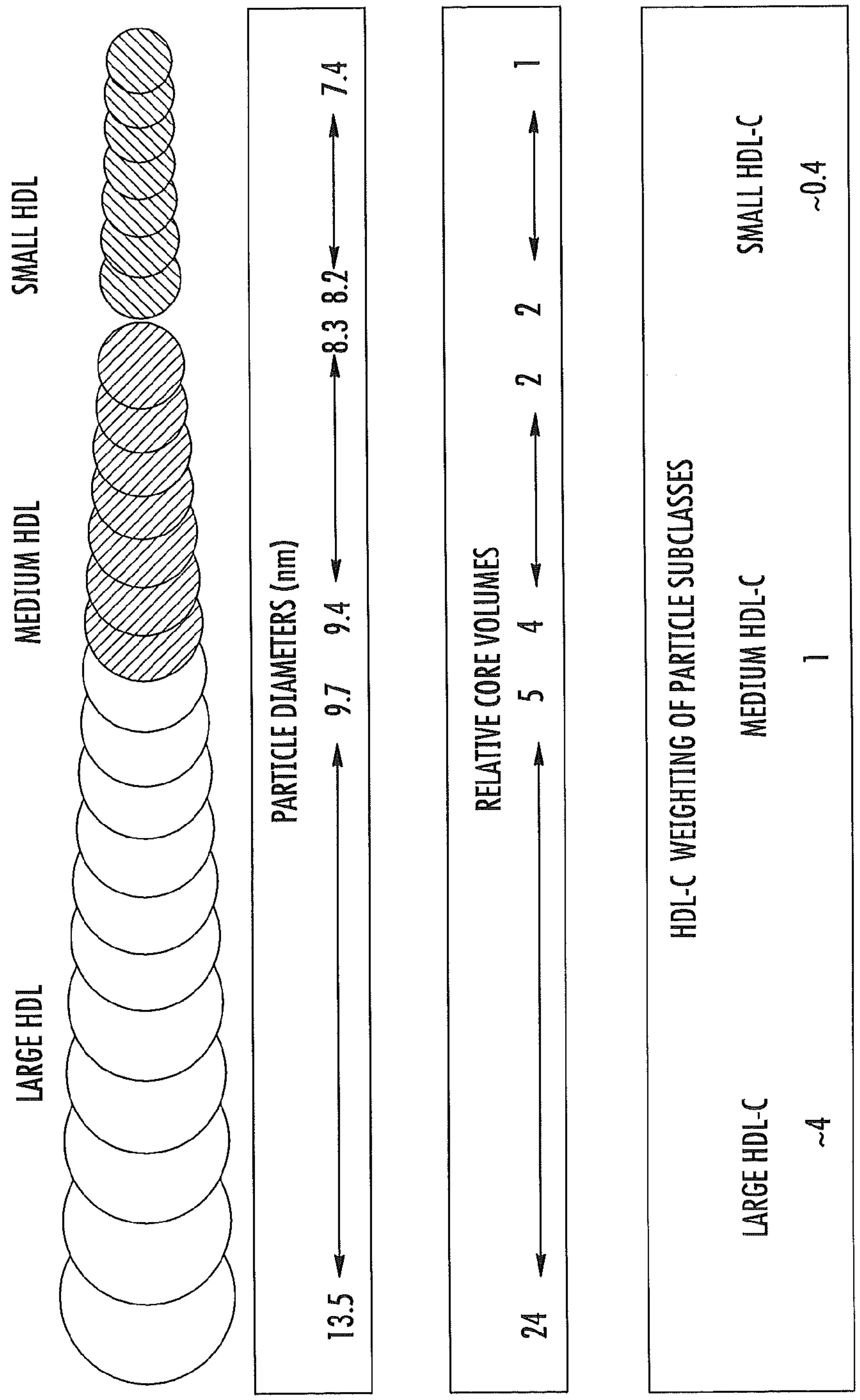
FIG. 5B is a schematic illustration of HDL particle size with respect to associated diameters, relative core volumes and HDL weighting of particle subclasses.

FIG. 5B is a schematic illustration showing that because larger HDL particles contain so much more cholesterol than smaller HDL particles, HDL-C as a risk biomarker gives much more weight to variations in the concentration of the large subpopulations and relatively undervalues differences in concentration of the smaller size subpopulations.

Figure 6:
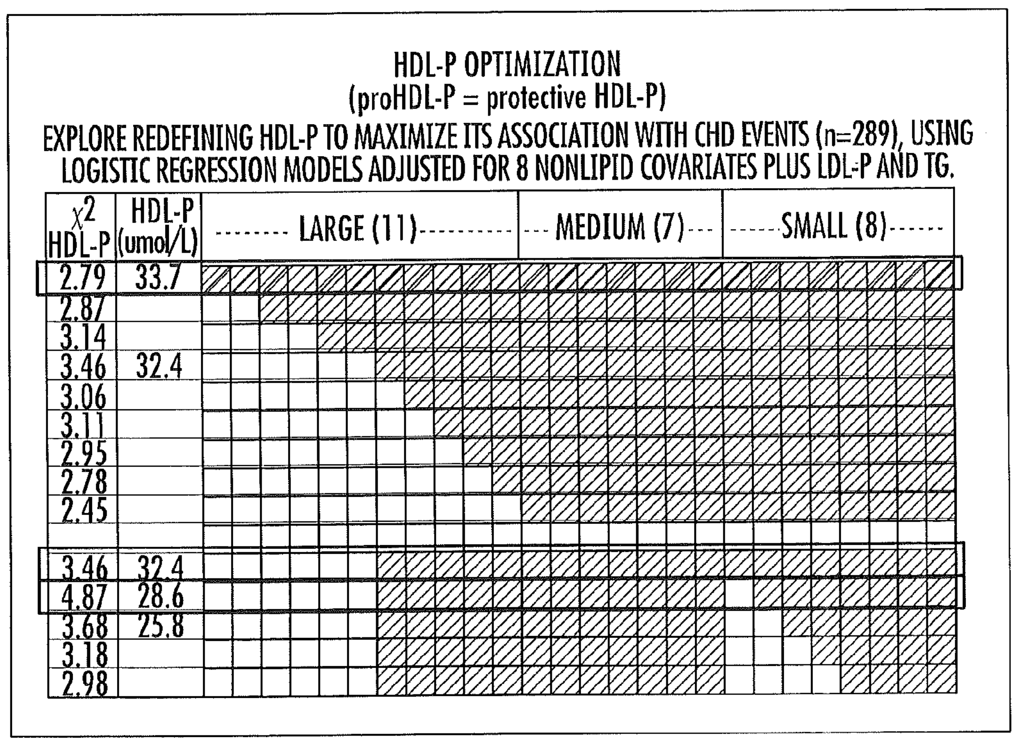
FIG. 6 is a chart showing the varying associations with CHD event risk of different groupings of the 26 HDL subpopulations to make alternate candidate versions of protective HDL-P according to embodiments of the present invention.

FIG. 6 illustrates a chart of the 26 different subpopulations of HDL-P. The estimated diameters of the 26 different subpopulations or components (H1-H26) are shown in Table 1. When the particle concentrations of all 26 of the HDL subpopulations are added together, as indicated by the shaded squares in the top row of the chart, it produces total HDL-P, the mean concentration of which is 33.7 μmol/L in the MESA study population. By omitting from total HDL-P, the concentrations of the various subpopulations indicated by the non-shaded squares in the chart, 12 other groupings of HDL-P are generated. The incremental amount of CHD risk prediction given by each of these alternate versions of HDL-P was assessed in logistic regression models adjusted for 8 non-lipid covariates and LDL-P and triglycerides (TG). The $\chi 2$ values in the left-most column of the chart give a quantitative assessment of how much incremental prediction was given by inclusion of each of the alternate HDL-P parameters in the regression model. Unexpectedly, it was found that omitting the 6 largest HDL subpopulations (H21-H26) made the HDL-P parameter more predictive of CHD risk, as indicated by the increase of the $\chi 2$ value to 3.46. As shown in the bottom section of the chart, an even more robust association of the HDL-P parameter was obtained by additionally omitting the H8 subpopulation. Stated differently, in some embodiments, the "protective HDL-P" number can exclude HDL subclass components at or above about 11 nm, e.g., with sizes between about 13.5 nm to about 11 nm.

TABLE 1

NMR HDL Subpopulation Groupings and Nomenclature

| HDL Deconvolution Model Components | | HDL Subpopulations | | | CHD Subclass Groupings* | |
|---|---|---|---|---|---|---|
| Component Name | Estimated Diameter (nm) | Component Name | Subpopulation Name | Estimated Diameter (nm) | Descriptive Name | Alternative Subclass Names |
| H1 | 7.4 | $H_{1-2}$ | HP1 | 7.4-7.5 | Very Small | $H_{1-2}$, $HP_1$, |
| H2 | 7.5 | | | | (<7.6 nm) | $HP_{VS}$ |
| H3 | 7.6 | $H_{3-5}$ | HP2 | 7.6-7.9 | Small | $H_{3-8}$, $HP_{2-3}$, |
| H4 | 7.8 | | | | (7.6-8.2 nm) | $HP_S$ |

TABLE 1-continued

NMR HDL Subpopulation Groupings and Nomenclature

| HDL Deconvolution Model Components | | HDL Subpopulations | | | CHD Subclass Groupings* | |
|---|---|---|---|---|---|---|
| Component Name | Estimated Diameter (nm) | Component Name | Subpopulation Name | Estimated Diameter (nm) | Descriptive Name | Alternative Subclass Names |
| H5 | 7.9 | | | | | |
| H6 | 8.0 | $H_{6-8}$ | HP3 | 8.0-8.2 | | |
| H7 | 8.1 | | | | | |
| H8 | 8.2 | | | | | |
| H9 | 8.3 | $H_{9-11}$ | HP4 | 8.3-8.5 | Medium + Large (8.6-10.9 nm) | $H_{9-20}$, $HP_{4-7}$, $HP_{ML}$ |
| H10 | 8.4 | | | | | |
| H11 | 8.5 | | | | | |
| H12 | 8.6 | $H_{12-14}$ | HP5 | 8.6-9.3 | | |
| H13 | 9.0 | | | | | |
| H14 | 9.2 | | | | | |
| H15 | 9.4 | $H_{15-17}$ | HP6 | 9.4-10.2 | | |
| H16 | 9.7 | | | | | |
| H17 | 10.0 | | | | | |
| H18 | 10.5 | $H_{18-20}$ | HP7 | 10.3-10.9 | | |
| H19 | 10.6 | | | | | |
| H20 | 10.8 | | | | | |
| H21 | 11.0 | $H_{21-23}$ | HP8 | 11.0-12.2 | Very Large (≥11.0 nm) | $H_{21-26}$, $HP_{8-9}$, $HP_{VL}$ |
| H22 | 11.5 | | | | | |
| H23 | 12.0 | | | | | |
| H24 | 12.5 | $H_{24-26}$ | HP9 | 12.3-13.5 | | |
| H25 | 13.0 | | | | | |
| H26 | 13.5 | | | | | |

*Subpopulation groupings as guided by CHD risk associations in MESA.

FIG. 7 illustrates different variants of protective HDL-P obtained by summing different HDL subpopulations as well as weighting them differentially, to assess their potential protective associations with CHD using Cox regression analyses in MESA (289 CHD events) adjusted for age, sex, ethnicity, smoking, SBP, hypertension treatment, BMI, diabetes (DM), log TG, and LDL-P. The different subpopulations can be summed to exclude H26-H21 (column 4), producing the P2-HDL-P parameter that includes all HDL particles with sizes ranging from about 7.3 nm to about 10.8 nm. Alternatively, protective HDL-P can be calculated by summing H7-1 and H20-9, excluding H8 and H26-21 (P1-HDL-P, column 3). In other embodiments, a defined weighting factor that increases the contribution of the smallest HDL particles (H7-H1) can be applied (in this example the weighting factor is 1.5) to produce the P3-HDL-P and P4-HDL-P variants (columns 5 and 6). In the bottom section of FIG. 7 are given the Model $\chi 2$ values from the 5 adjusted Cox regression models that included a different variant of HDL-P. The weakest prediction was given by "regular" total HDL-P (sum of H1 through H26) and the strongest by P3-HDL-P.

FIG. 8 is a chart that identifies potential NP HDL-P parameters ("A-HDL-Ps"). When comparing two groupings of large HDL subclass components, 1426-H21 versus H24-H23, both show positive risk associations with CHD. A risk assessment can be generated that considers both NP HDL-P and protective HDL-P.

Figure 9A:
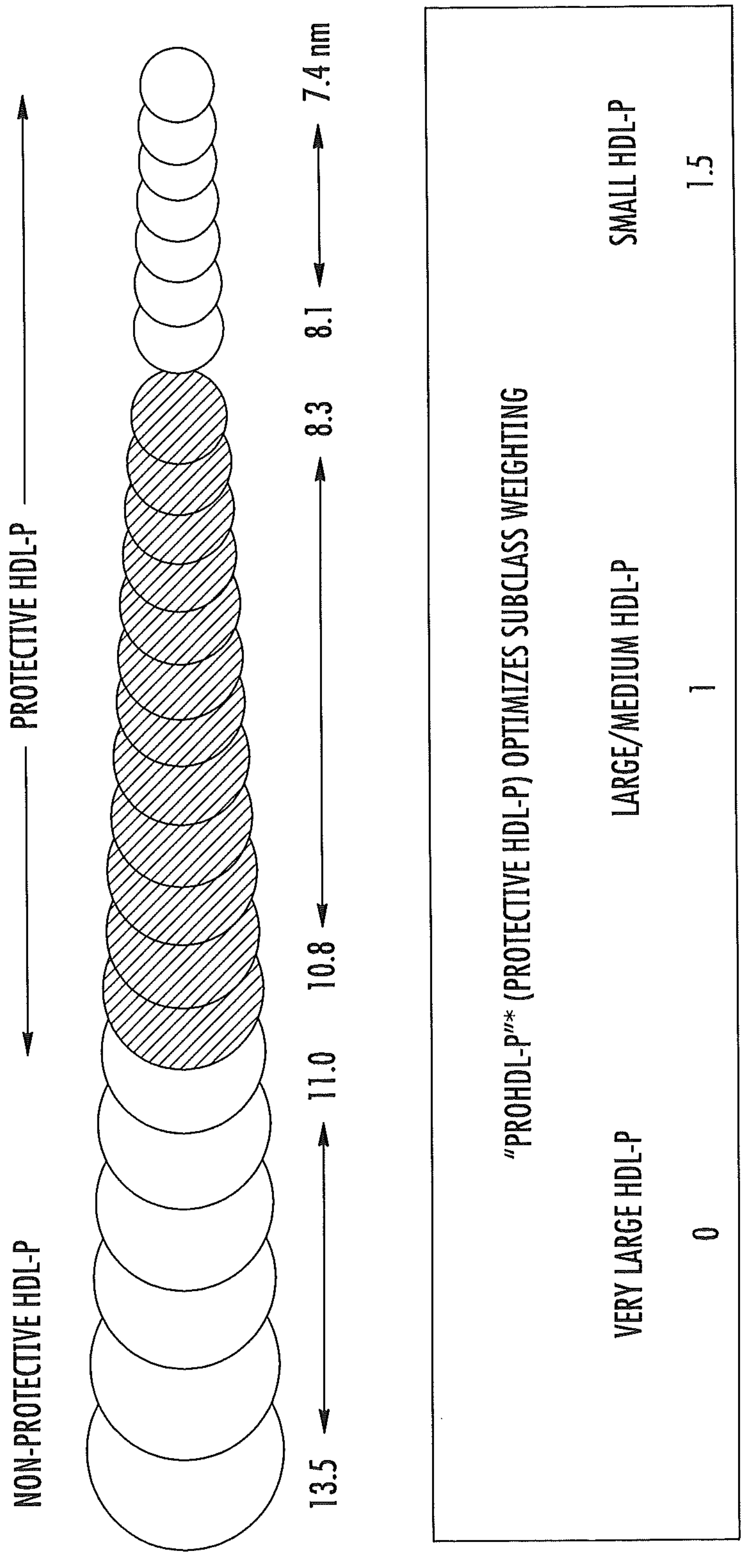
FIG. 9A is a schematic illustration of HDL-P indicating particle sizes associated with non-protective HDL and protective HDL, and with exemplary protective HDL-P weighting using the "P3" weighting of FIG. 7 according to embodiments of the present invention.

FIG. 9A is a schematic illustration of HDL-P indicating particle sizes associated with non-protective HDL and protective HDL, and with exemplary protective HDL-P weighting using the "P3" weighting of FIG. 7 according to embodiments of the present invention.

FIG. 9B is a chart of different HDL parameters and associated subclass weighting and CHD prediction in MESA derived from Cox regression models adjusted for age, sex, ethnicity, smoking, SBP, hypertension treatment, BMI, diabetes, log TG, and LDL-P according to embodiments of the present invention.

FIG. 9C is a chart that illustrates that the protective HDL-P measurements can provide clinically meaningful risk assessments over LDL-P alone, LDL-P and TG, LDL-P, TG and HDL-C, and LDL-P, TG and total HDL-P number measurements. This chart reflects logistic regression models for CHD events (n=289) adjusted for age, sex, race, smoking, systolic blood pressure, hypertension treatment (HT-Nrx), BMI and diabetes status.

Figure 10:
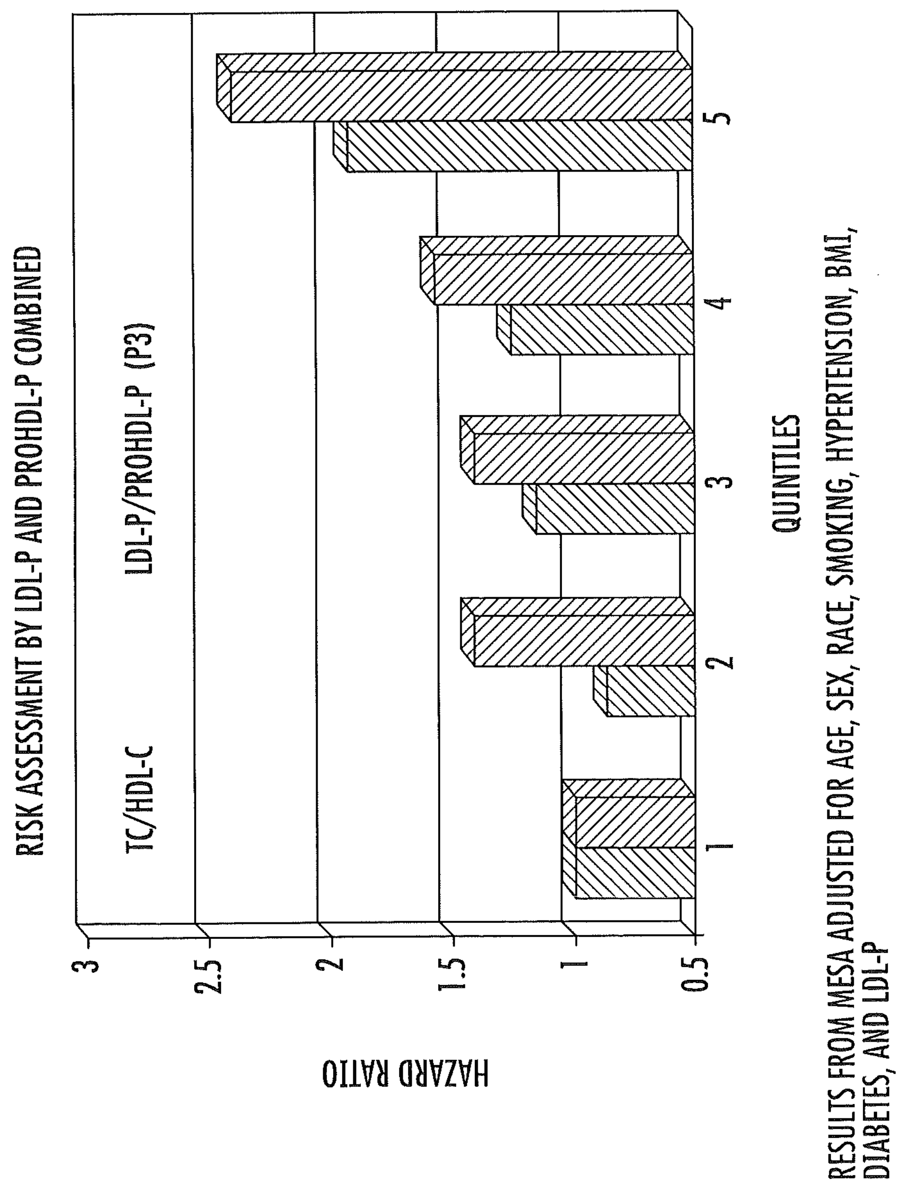
FIG. 10 is a graph of CHD risk (as given by Hazard Ratio) as a function of the LDL-P to protective HDL-P ratio (using the "P3" model of FIG. 7) and total cholesterol (TC) to HDL-C ratio by quintiles.

FIG. 10 is a graph of CHD risk (as given by Hazard Ratio) as a function of quintiles of either LDL-P to protective HDL-P (using the "P3" model of FIG. 7) ratio or total cholesterol (TC) to HDL-C ratio.

Figure 11:
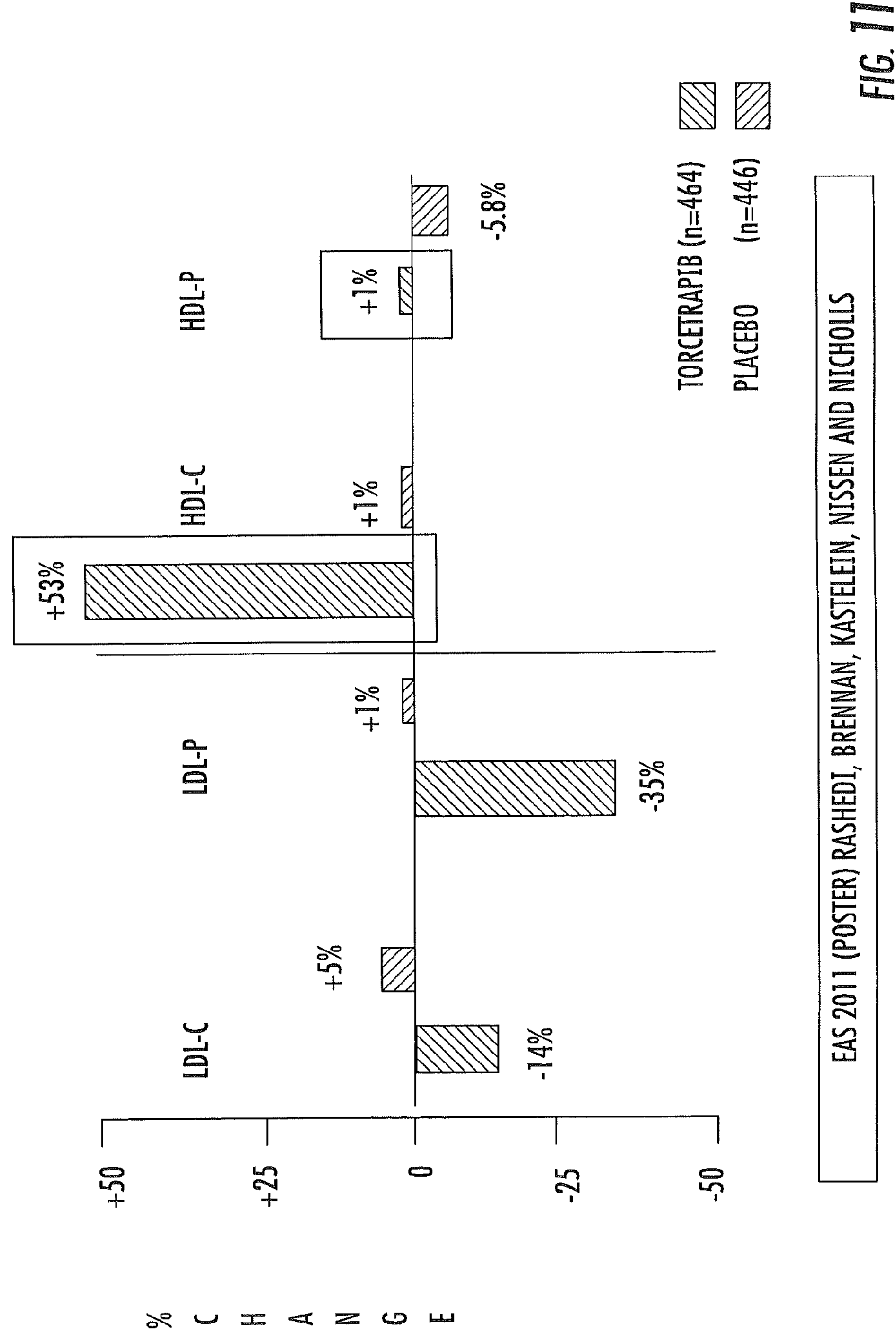
FIG. 11 is a graph of percent change of several lipid and NMR-derived lipoprotein particle parameters illustrating the impact of treatment by a CETP inhibitor (torceptrapib) on these parameters according to embodiments of the present invention.

Different therapies that increase HDL-C by the same amount may not increase the HDL subclasses proportionately. Some drugs, for example, increase HDL-C mainly by increasing the number of small HDL particles (such as those in the fibrate class). Others increase mainly large HDL-P. The HDL particle subclass concentrations can change differentially with different therapies, indicating potentially greater or lesser clinical benefit and may provide enhanced protocols for evaluating therapeutic efficacy. FIG. 11 shows the impact of a CETP inhibitor (torceptrapib) on NMR-derived lipoprotein particle parameters. See, e.g., Rashedi N, Brennan D, Kastelein J J, Nissen S E, Nicholls S. 2011 *European Atherosclerosis Society meeting presentation.*

The protective HDL-P and NP-HDL-P measurements can provide more reliable data on therapies, clinical trials and the like about the potential performance of drugs aimed at reducing CHD. That is, instead of merely determining whether a drug can increase HDL-C, it may be desirable to evaluate whether the drug increases the more discriminating protective HDL-P number and/or increases or decreases the NP-HDL-P number.

Figure 12:
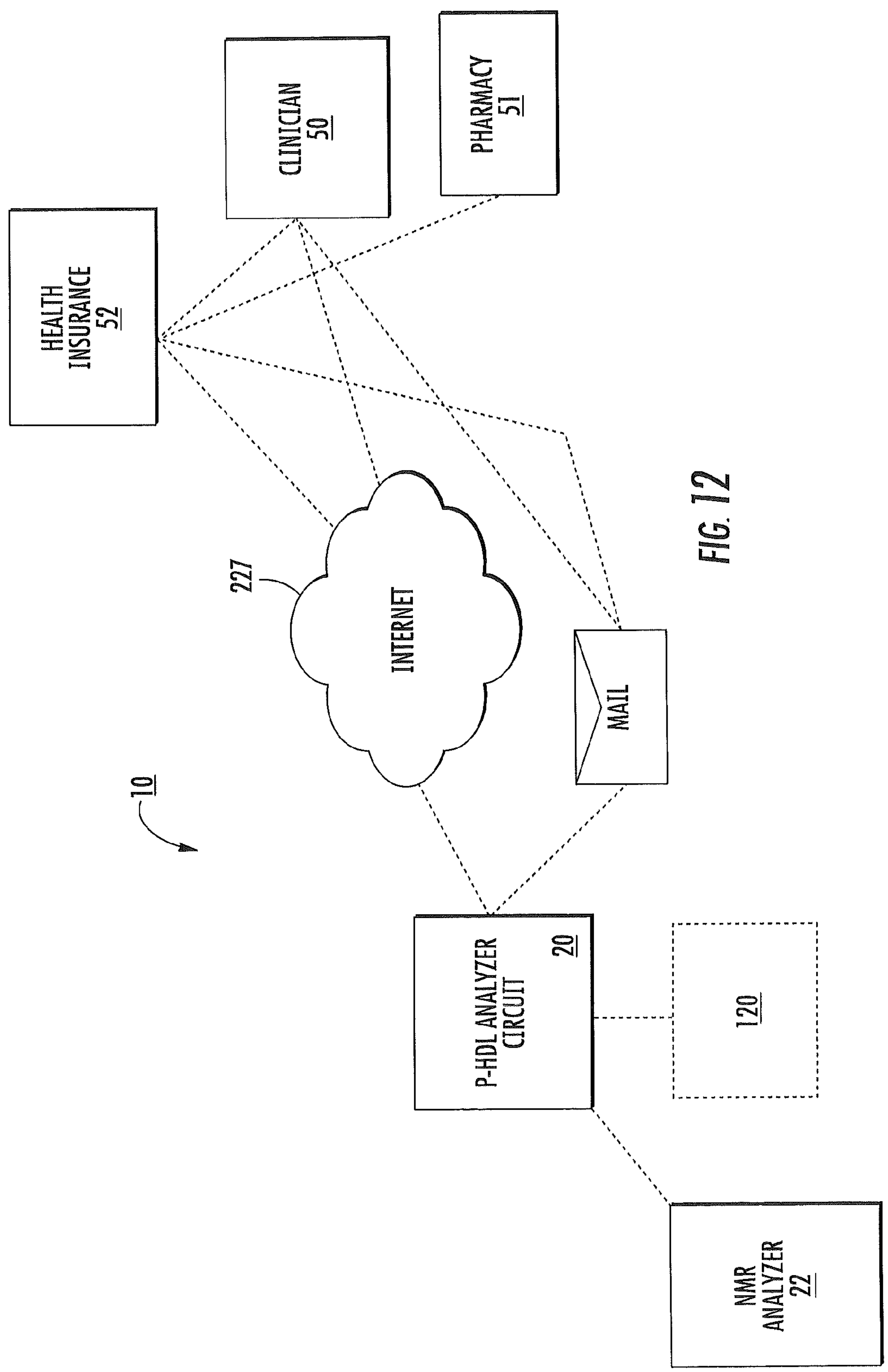
FIG. 12 is a schematic illustration of a system for analyzing protective HDL-P according to embodiments of the present invention.

Referring now to FIG. 12, it is contemplated that the protective (and optionally non-protective) HDL-P analysis can be carried out using a system 10 with an NMR clinical analyzer 22 as described, for example, with respect to FIGS. 13 and 14 below and/or in U.S. Pat. No. 8,013,602, the contents of which are hereby incorporated by reference as if recited in full herein.

The system 10 can include a HDL-P analysis circuit 20 that can be on-board the analyzer 22 or remote from the analyzer 22. If the latter, the analysis module or circuit 20 can reside totally or partially on a server 150. The server 150 can be provided using cloud computing which includes the provision of computational resources on demand via a computer network. The resources can be embodied as various infrastructure services (e.g. compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and test data.

The results of the analysis can be transmitted via a computer network, such as the Internet, via email or the like to a clinician site 50, to a health insurance agency 52 or a pharmacy 51. The results can be sent directly from the analysis site or may be sent indirectly. The results may be printed out and sent via conventional mail. This information can also be transmitted to pharmacies and/or medical insurance companies, or even patients that monitor for prescriptions or drug use that may result in an increase risk of an adverse event. The results can be sent to a patient via email to a "home" computer or to a pervasive computing device such as a smart phone or notepad and the like. The results can be as an email attachment of the overall report or as a text message alert, for example.

Figure 13:
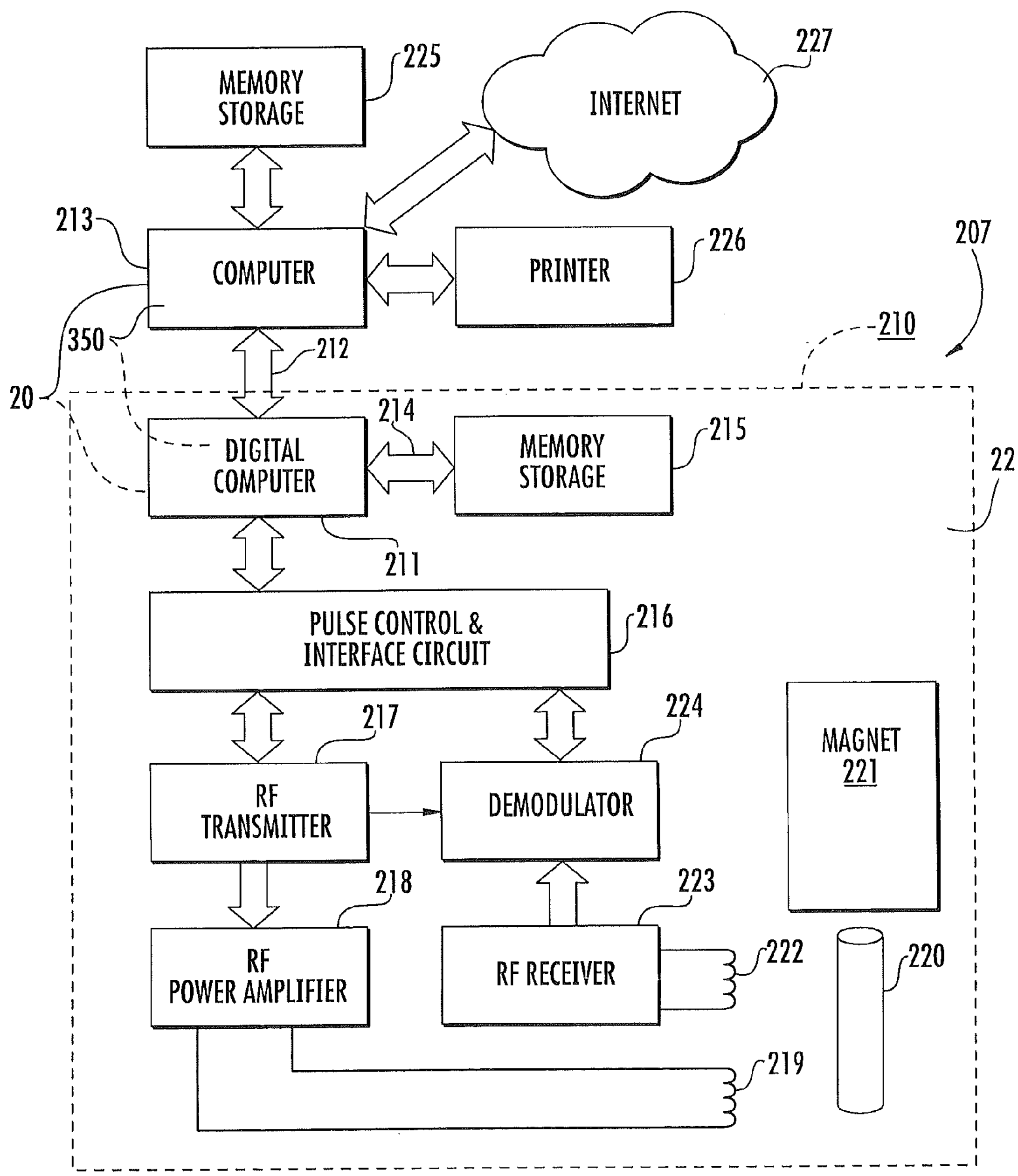
FIG. 13 is a schematic illustration of a NMR spectroscopy apparatus according to embodiments of the present invention.

Referring now to FIG. 13, a system 207 for acquiring and calculating the lineshape of a selected sample is illustrated. The system 207 includes an NMR spectrometer 22 for taking NMR measurements of a sample. In one embodiment, the spectrometer 22 is configured so that the NMR measurements are conducted at 400 MHz for proton signals; in other embodiments the measurements may be carried out at 360 MHz or other suitable frequency. Other frequencies corresponding to a desired operational magnetic field strength may also be employed, typically between about 200 MHz-900 MHz. Typically, a proton flow probe is installed, as is a temperature controller to maintain the sample temperature at 47+/−0.5 degrees C. The spectrometer 22 is controlled by a digital computer 214 or other signal processing unit. The computer 211 should be capable of performing rapid Fourier transformations. It may also include a data link 212 to another processor or computer 213, and a direct-memory-access channel 214 which can connects to a hard memory storage unit 215.

The digital computer 211 may also include a set of analog-to-digital converters, digital-to-analog converters and slow device I/O ports which connect through a pulse control and interface circuit 216 to the operating elements of the spectrometer. These elements include an RF transmitter 217 which produces an RF excitation pulse of the duration, frequency and magnitude directed by the digital computer 211, and an RF power amplifier 218 which amplifies the pulse and couples it to the RF transmit coil 219 that surrounds sample cell 220. The NMR signal produced by the excited sample in the presence of a 9.4 Tesla polarizing magnetic field produced by superconducting magnet 221 is received by a coil 222 and applied to an RF receiver 223. The amplified and filtered NMR signal is demodulated at 224 and the resulting quadrature signals are applied to the interface circuit 216 where they are digitized and input through the digital computer 211. The lipoprotein measurement and/or protective and/or non-protective HDL-P analyzer circuit 20 or module 350 (FIGS. 12-14) or circuit 20 can be located in one or more processors associated with the digital computer 211 and/or in a secondary computer 213 or other computers that may be on-site or remote, accessible via a worldwide network such as the Internet 227.

After the NMR data are acquired from the sample in the measurement cell 220, processing by the computer 211 produces another file that can, as desired, be stored in the storage 215. This second file is a digital representation of the chemical shift spectrum and it is subsequently read out to the computer 213 for storage in its storage 225 or a database associated with one or more servers. Under the direction of a program stored in its memory, the computer 213, which may be a personal, laptop, desktop, workstation, notepad or other computer, processes the chemical shift spectrum in accordance with the teachings of the present invention to generate a report which may be output to a printer 226 or electronically stored and relayed to a desired email address or URL. Those skilled in this art will recognize that other output devices, such as a computer display screen, notepad, smart phone and the like, may also be employed for the display of results.

It should be apparent to those skilled in the art that the functions performed by the computer 213 and its separate storage 225 may also be incorporated into the functions performed by the spectrometer's digital computer 211. In such case, the printer 226 may be connected directly to the digital computer 211. Other interfaces and output devices may also be employed, as are well-known to those skilled in this art.

Certain embodiments of the present invention are directed at providing methods, systems and/or computer program products that use protective and/or non-protective HDL-P numbers that may be particularly useful in automated screening tests and/or risk assessment evaluations for CAD screening of in vitro biosamples.

As will be appreciated by one of skill in the art, the present invention may be embodied as an apparatus, a method, data or signal processing system, or computer program product. Accordingly, the present invention may take the form of an entirely software embodiment, or an embodiment combining software and hardware aspects. Furthermore, certain embodiments of the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, but is not limited to, an electronic, magnetic, optical, electromagnetic, infrared, or semiconductor system, apparatus, device, or propagation medium. More specific examples (a nonexhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk, Python, Labview, C++, or VisualBasic. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The flowcharts and block diagrams of certain of the figures herein illustrate the architecture, functionality, and operation of possible implementations of analysis models and evaluation systems and/or programs according to the present invention. In this regard, each block in the flow charts or block diagrams represents a module, segment, operation, or portion of code, which comprises one or more executable instructions for implementing the specified logical function(s). It should also be noted that in some alternative implementations, the functions noted in the blocks might occur out of the order noted in the figures. For example, two blocks shown in succession may in fact be executed substantially concurrently or the blocks may sometimes be executed in the reverse order, depending upon the functionality involved.

Figure 14:
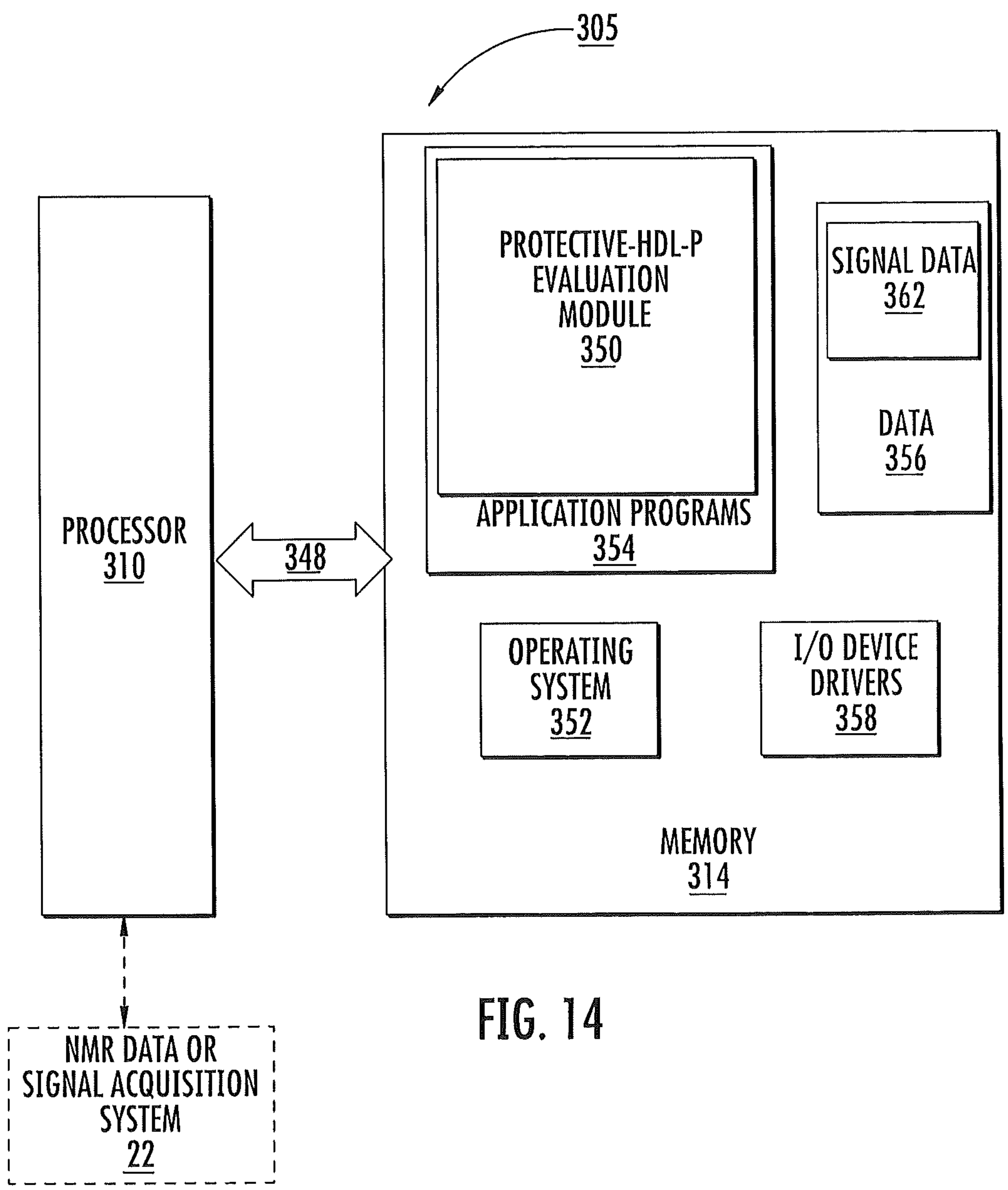
FIG. 14 is a schematic diagram of a data processing system according to embodiments of the present invention.

FIG. 14 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 14, the memory 314 may include several categories of software and data used in the data processing system 305: the operating system 352; the application programs 354; the input/output (I/O) device drivers 358; a protective HDL-P Evaluation Module 350; and the data 356. The Protective HDL-P Evaluation Module 350 can sum concentrations of defined subpopulations of HDL to define the protective and/or non-protective HDL-P number.

The data 356 may include signal (constituent and/or composite spectrum lineshape) data 362 which may be obtained from a data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000 or WindowsXP from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and can include at least one application, which supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the Module 350 being an application program in FIG. 14, as will be appreciated by those of skill in the art, other configurations may also be utilized while still benefiting from the teachings of the present invention. For example, the protective HDL-P Module 350 may also be incorporated into the operating system 352, the I/O device drivers 358 or other such logical division of the data processing system 305. Thus, the present invention should not be construed as limited to the configuration of FIG. 14, which is intended to encompass any configuration capable of carrying out the operations described herein.

In certain embodiments, the Module 350 includes computer program code for providing a measure of protective HDL and a measure of NP HDL which may be used to indicate whether therapy intervention is desired and/or track efficacy of a therapy.

Figure 15:
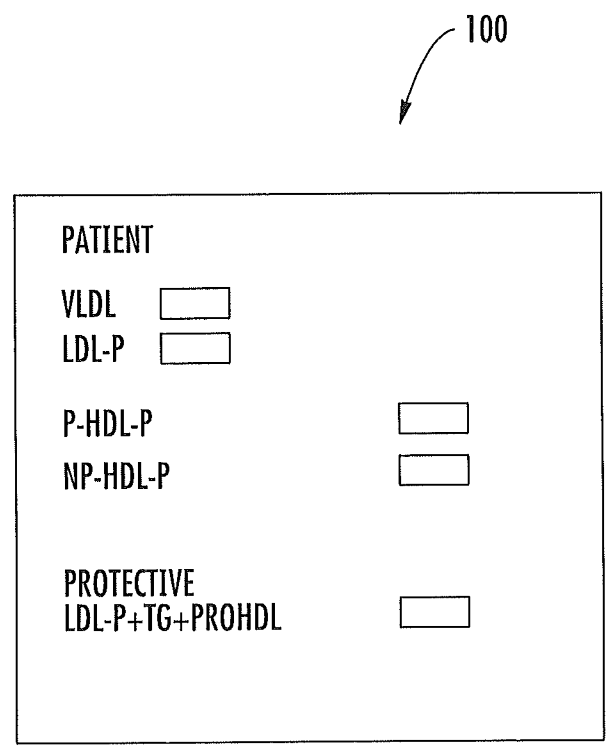
FIG. 15 is an example of a patient report that includes a protective HDL-P number according to embodiments of the present invention.

FIG. 15 is a schematic illustration of an exemplary patient test report 100 that can include various lipoprotein parameters such as LDL-P, VLDL and the protective HDL-P (and optionally the non-protective HDL-P). The protective HDL-P number can be presented with a risk assessment data correlated to population norms, typical ranges, and/or degree of risk.

Figure 16:
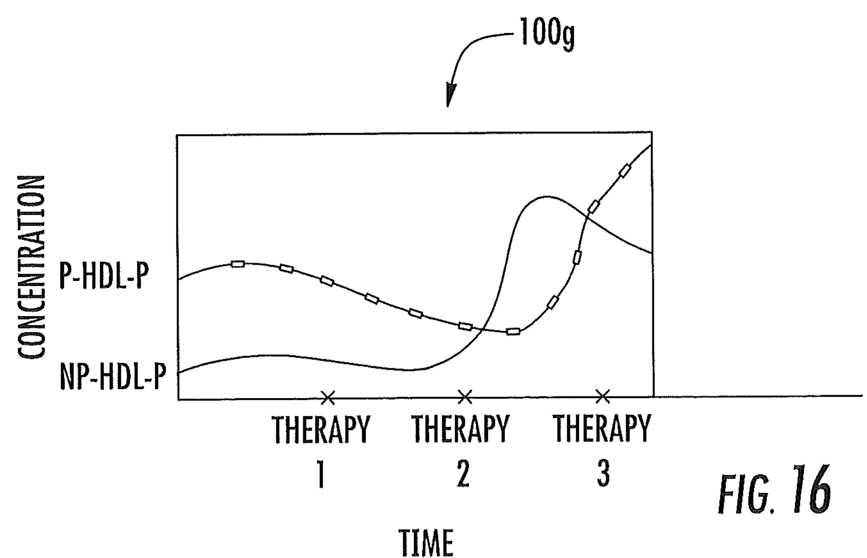
FIG. 16 is an example of a graph that can monitor change in one or both protective HDL-P (Pro-HDL-P) and non-protective HDL-P (NP-HDL-P) over time to evaluate a patient's metabolic status, change, or clinical efficacy of a therapy or even used for clinical trials and the like according to embodiments of the present invention.

FIG. 16 illustrates that a graph of protective HDL-P (P-HDL-P) and/or non-protective HDL-P (NP HDL-P) can be provided to illustrate a change in patient metabolic HDL function over time due to age, medical intervention or a therapy according to some embodiments. Tracking both of these parameters may provide better clinical indicators of efficacy of a therapy and/or a better risk predictor for CHD for patients.

As shown in FIG. 16, the protective HDL-P analysis can be used to monitor a patient over time to correlate known start or use of a drug or other therapy to evaluate whether HDL function has been altered and/or whether protective (or non-protective) HDL-P has been increased or decreased using such therapy. It may be a therapeutic goal to increase protective HDL-P while also decreasing NP-HDL.

Future drugs or uses of known drugs can be identified, screened or tested in patients identified using the protective and/or non-protective HDL-P number evaluations.

Figure 17:
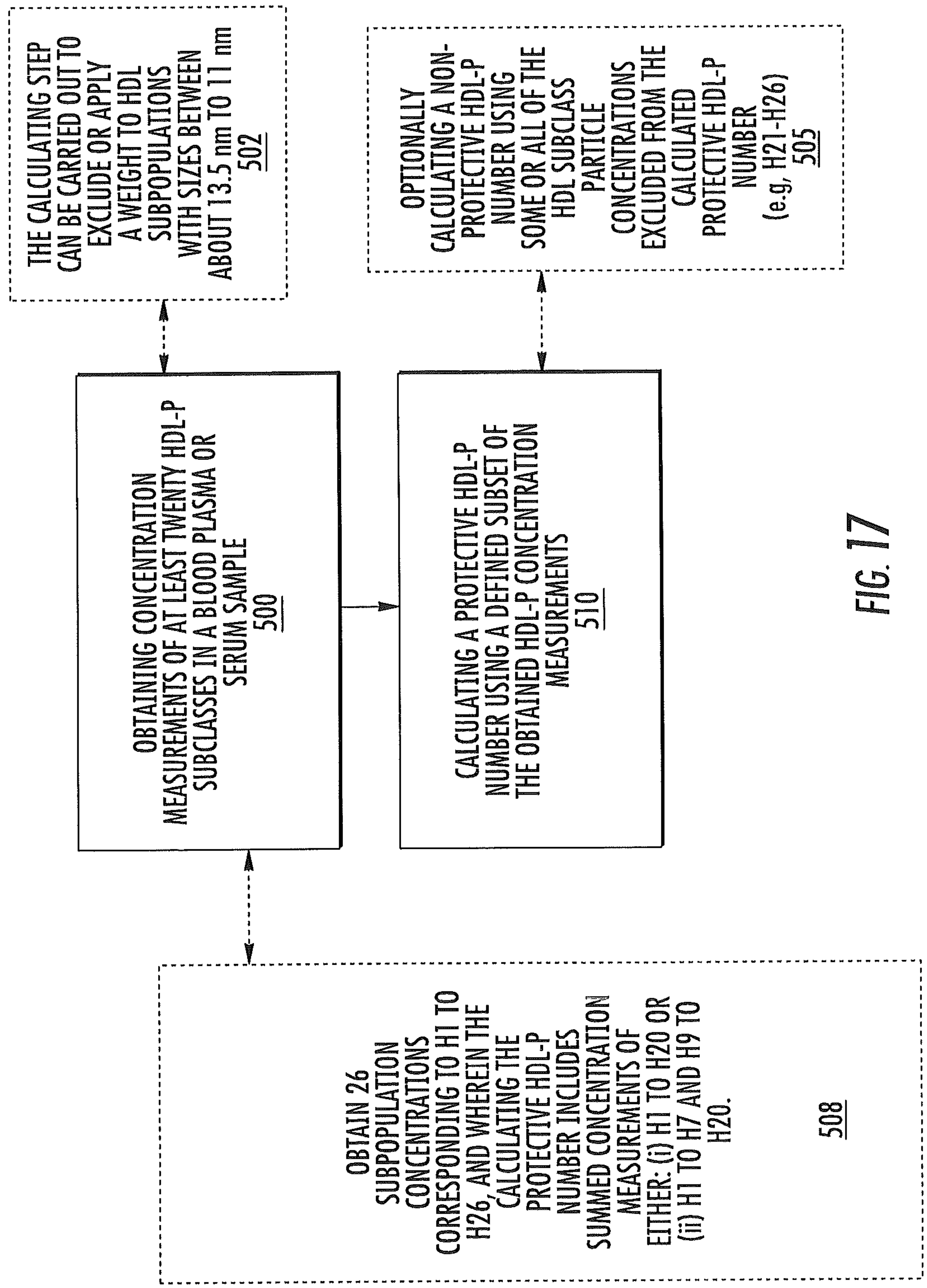
FIG. 17 is a flow chart of exemplary actions that can be used to calculate protective and/or non-protective HDL-P according to embodiments of the present invention.

FIG. 17 is a flow chart of exemplary operations that can be used to carry out embodiments of the invention for determining protective high density lipoprotein particle (HDL-P) numbers. Concentration measurements of at least twenty subpopulations of HDL-P subclasses in a blood plasma or serum sample can be obtained (block 500). A protective HDL-P number can be calculated using a defined subset of the obtained HDL-P concentration measurements (block 510).

The calculating step can be carried out to exclude HDL subpopulations with sizes between about 13.5 nm to about 11 nm and/or sizes about 11 nm and above (block 502).

Optionally, a non-protective HDL-P number can be calculated using some or all of the HDL subclass particle concentrations excluded from the calculated protective HDL-P number (block 505).

Twenty six subpopulation concentrations can be obtained, corresponding to H1 to H26, and the calculating the protective HDL-P number can be carried out using summed concentration measurements of either: (i) H1 to H20 or (ii) H1 to H7 and H9 to H20 (block 508).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method of determining the risk of coronary heart disease (CHD) for a subject, comprising:

providing a sample from a subject;

measuring by a NMR spectrometer at least twenty HDL-P subpopulations in the sample;

calculating, using at least one processor, a protective HDL-P number using either (i) a defined subset of the HDL-P subpopulation concentration measurements, wherein the defined subset excludes HDL-P subpopulations with particles sizes 11 nm and above; or (ii) a zero or defined weighting factor below 1 for HDL-P concentration measurements for HDL-P subpopulations with particle sizes 11 nm and above; and determining the CHD risk for the subject using the protective HDL-P number.

2. The method of claim 1, wherein the calculating step is carried out to exclude HDL-P subpopulations with particle sizes between about 13.5 nm to 11 nm.

3. The method of claim 1, further comprising calculating a non-protective HDL-P number using some or all of the HDL-P subpopulation concentrations excluded from the calculated protective HDL-P number.

4. The method of claim 1, wherein the measuring step is carried out to obtain 26 subpopulation concentrations corresponding to H1 to H26, and wherein the calculating the protective HDL-P number includes summed concentration measurements of either: (i) H1 to H20 or (ii) H1 to H7 and H9 to H20.

5. The method of claim 1, wherein the measuring step includes measuring at least 26 discrete subpopulation concentrations of HDL-P with particle sizes between about 7 nm to about 14 nm, corresponding to H1 to H26, and wherein the calculating the protective HDL-P number includes summing H1 to H7 concentrations, then applying a defined first weight above 1 to the summed concentration of H1 to H7 and summing the weighted H1-H7 concentration with a sum of H9-H20 concentrations.

6. The method of claim 1, wherein the calculating step further comprises generating a protective CHD lipoprotein parameter using the protective HDL-P number and a low density lipoprotein particle (LDL-P) number; and wherein the determining the CHD risk for the subject is based on the protective CHD lipoprotein parameter.

7. The method of claim 1, wherein the sample is an in vitro blood plasma or serum sample.

8. The method of claim 1, wherein the calculating step is carried out using a subset of HDL-P subpopulation with particles sizes between about 7 nm and 11 nm.

9. A method of claim 1 further comprising generating a patient report comprising: a plurality of lipoprotein measurements including a non-protective or atherogenic low density lipoprotein particle number (LDL-P), a protective high density lipoprotein particle (HDL-P) number in concentration units and a non-protective HDL-P number in concentration units.

10. The method of claim 1, wherein the determining the CHD risk for the subject is based on the ratio of a number of lipoprotein density lipoprotein particles (LDL-P) to the number of the protective HDL-P of the subject.

11. A method for determining a risk of CHD for a subject, comprising:

providing a sample from the subject;

measuring greater than 20 NMR derived concentration measurements of subpopulations of small, medium and large high density lipoprotein (HDL) subclasses of the sample;

summing, using at least one processor, HDL particle concentration measurements of substantially all HDL small, medium and large high density lipoprotein (HDL) subclasses having particle sizes between about 7.3 nm to about 10.8 nm;

defining a protective HDL-P number based on the summing step; and determining the risk of CHD using the protective HDL-P number.

12. The method of claim 11, further comprising: applying a zero or a defined reduced weight to or excluding concentration measurements of large HDL-P subpopulations with particle sizes of 11 nm or greater; applying an increased weighting factor to the concentration measurements of small HDL-P subpopulations with particles sizes less than 11 nm before the summing step, then using the weighted small and large HDL particle concentrations in the summing step.

13. The method of claim 11, further comprising calculating a non-protective HDL-P number using concentrations of large HDL-P subpopulations with particle sizes of 11 nm and above.

14. A computer program product for determining the risk of CHD for a subject, the computer program product comprising: a non-transitory computer readable storage medium having computer readable program code embodied in the medium, the computer-readable program code comprising:

computer readable program code that obtains from a NMR spectromenter concentration measurements of at least twenty HDL-P subpopulations in a sample from the subject;

computer readable program code that calculates a protective HDL-P number using a defined subset of the obtained HDL-P subpopulation concentration measurements, wherein the defined subset excludes HDL-P subpopulations with particle sizes 11 nm and above or using a zero or defined weighting factor below 1 for HDL-P subpopulation concentration measurements for HDL-P with particle sizes above 11 nm; and computer readable program code that determines the risk of CHD for the subject using the protective HDL-P number.

15. The computer program product of claim 14, wherein the computer program code that calculates is configured to exclude or apply a zero weight to HDL-P subpopulations with particle sizes between about 13.5 nm to 11 nm.

16. The computer program product of claim 14, further comprising computer program code that calculates a non-protective HDL-P number using HDL-P subpopulation concentrations excluded from or given a zero weight in the calculated protective HDL-P number.

17. The computer program product of claim 14, wherein the computer program code that obtains 26 subpopulation concentrations corresponding to H1 to H26, and wherein the computer program code that calculates the protective HDL-P number is configured to sum concentration measurements of either: (i) H1 to H20 or (ii) H1 to H7 and H9 to H20.

18. A system for obtaining lipoprotein constituent data to assess anti-atherogenic protection and/or CHD risk, comprising:

an NMR spectrometer for acquiring at least one NMR spectrum of an in vitro blood plasma or serum sample; and a controller in communication with the NMR spectrometer, the controller comprising at least one processor configured to (i) obtain concentration measurements of at least twenty subpopulations of HDL-P subpopulations in a blood plasma or serum sample and (ii) calculate a protective HDL-P number using (a) defined subset of the obtained HDL-P concentration measurements, wherein the defined subset excludes HDL-P subpopulations with particles sizes 11 nm and above; or (b) a zero or defined weighting factor below 1 for HDL-P concentration measurements for HDL-P subpopulations with particle sizes of 11 nm and above.

* * * * *